United States Patent [19]

Molitor et al.

[11] Patent Number: 4,782,503
[45] Date of Patent: Nov. 1, 1988

[54] DENTAL X-RAY DIAGNOSTIC INSTALLATION

[75] Inventors: Dieter Molitor, Bürstadt; Werner Günther, Bensheim, both of Fed. Rep. of Germany

[73] Assignee: Siemens Aktiengesellschaft, Berlin and Munich, Fed. Rep. of Germany

[21] Appl. No.: 897,799

[22] Filed: Aug. 19, 1986

[30] Foreign Application Priority Data

Aug. 23, 1985 [DE] Fed. Rep. of Germany ....... 3530234

[51] Int. Cl.⁴ .............................. A61B 6/14; A61B 6/02
[52] U.S. Cl. ....................................... 378/169; 378/38; 378/170
[58] Field of Search ............... 378/38, 39, 40, 167, 378/168, 169, 170, 177, 179, 180, 205, 208

[56] References Cited

U.S. PATENT DOCUMENTS

| | | | |
|---|---|---|---|
| 2,720,708 | 10/1955 | Snell | 33/174 |
| 3,539,805 | 11/1970 | Shiller et al. | 378/38 |
| 3,930,507 | 1/1976 | Berman | 128/345 |
| 4,200,798 | 4/1980 | Neuendorf et al. | 250/439 |
| 4,694,478 | 9/1987 | Delnon | 378/38 |

FOREIGN PATENT DOCUMENTS

| | | |
|---|---|---|
| 0002706 | 7/1979 | European Pat. Off. . |
| 898793 | 10/1953 | Fed. Rep. of Germany . |
| 1130687 | 5/1962 | Fed. Rep. of Germany . |
| 3513455 | 10/1986 | Fed. Rep. of Germany . |

OTHER PUBLICATIONS

Sales Brochure Entitled: "Minimize X-ray Dosage Maximize Image Quality ... ", Orthopantomograph 10, 1985.

Primary Examiner—Carolyn E. Fields
Assistant Examiner—Joseph A. Hynds
Attorney, Agent, or Firm—Hill, Van Santen, Steadman & Simpson

[57] ABSTRACT

In order to be able to produce congruent panoramic strip exposures of a jaw of a patient with a dental x-ray diagnostic installation, the patient's head must be positioned by means of a forehead support, which is adjustable only in a horizontal plane, and by means of a seating part which is rigidly arranged on a carrier in the device. The seating part contains an arrangement for forming a seating surface for engaging the upper jaw of the patient so that the seating surface engages a subnasal point of the jaw for those patients who have no teeth or only part of their teeth and a second seating type surface for those patients having a full set of teeth.

16 Claims, 7 Drawing Sheets

DENTAL X-RAY DIAGNOSTIC INSTALLATION

BACKGROUND OF THE INVENTION

The present invention is directed to a dental x-ray diagnostic installation or apparatus for producing congruent panorama strip exposures of the jaw of a patient. The apparatus includes a rotary unit, which carries a radiation source and a film cassette and has at least two positioning members for positioning the patient's head with reference to the rotary unit. One of these positioning members is a forehead support adjustable in a horizontal direction and the device or apparatus includes a display arrangement for indicating at least the adjusted position of the forehead support.

In a known x-ray diagnostic installation or apparatus, an example is disclosed in the sales brochure for ORTHOPANTOMOGRAPH a forehead support for positioning the patient's head on one hand, and also a chin support with a bite-down part are provided. Chin supports and forehead supports are horizontally adjustable in the direction towards a pillar or stand on which the rotary unit comprising the x-ray source and a film cassette are pivotably mounted. In order to be able to correctly position the patient's head with reference to the centricity and inclination (Frankfurter Horizontal), a light beam localizer or positioner is also provided so that the correct inclination of the skull on the one hand, and also the center of the face are capable of being set or, respectively, monitored with the light beam localizer. The patient position, which has been set, can be read from a digital display.

Both what is referred to as a standard exposure, for example exposures of the upper jaw and lower jaw, as well as what is referred to as sine exposures, for example exposures of the superior maxillary cavities as well as exposures of the maxillary joint, can be produced with such an apparatus. The adjustably arranged chin support is provided with a small, pivotable retaining rod or with a bite-down part for fixing the front teeth of the jaw. Even though it is possible to produce reproducible exposures with the apparatus set forth because the values of the forehead support position and those of the position of the chin position have been recorded or noted and these values are then re-set when another exposure of the same patient is to be made, the adjustment precision obtainable with this apparatus nonetheless does not correspond to today's demands with respect to a deviation of less than 1 mm for the later exposure with respect to the original exposure.

Such precise reproducible exposures cannot be achieved with other apparatuses which have been disclosed in a patent literature, for example U.S. Pat. No. 2,720,708 and German patent No. 898,793. These are affected by even a further disadvantage because the adjustment of the patient's head is relatively time consuming and complicated. For example, in the device of the German patent No. 898,793, four positioning members must be adjusted. The apparatus contains an annular shackle on which two pins are located for introduction into the orifices of the auditory passages. The shackle also adjustably supports a slide part, which can be applied to the transition between the upper lip and the lower root of the nasal septum. Also mounted in the shackle is an indicator pin in which the point of entry of the x-ray can be marked on the patient's skin by means of a colored dot. The shackle and the four positioning members or, respectively, their mounts are provided with scales in the form of line markings which must be read and noted after the patient has been adjusted.

In the apparatus of U.S. Pat. No. 2,720,708, which is not able to make panorama strip exposures of the jaw of a patient, first and second positioning members are provided with the first being a bite-down part for the front teeth and the second being a cap which can be placed on the patient's head. These positioning members are suspended in an adjustable fashion in a number of planes and each of the adjustment elements is provided with scales.

The two known apparatuses offer no possibility of carrying out initially cited different types of exposures, for example lower jaw, upper jaw, sinus and maxillary joint exposures for either a patient with teeth or for a patient who is without teeth.

SUMMARY OF THE INVENTION

The present invention is directed to the object of improving an x-ray diagnostic apparatus for producing congruent panoramic strip exposures of the jaw of a patient to such an extent that repeat exposures having smaller deviations than hitherto can be produced with a relatively simple adjustment technique so that a positioning possibility should be established for patients having teeth as well as patients without teeth and patients having only part of their teeth.

In order to achieve this object, it is proposed in accordance with the present invention that a second positioning member or means is a rest or seating part rigidly arranged in a defined position in a carrier connected to the rotary unit and that this seating part contains means forming contact or seating surfaces for exposures for patients having teeth, namely exposures for at least the front teeth and means for forming seating surfaces for exposures of partially toothed or, respectively, toothless patients by providing a sub-nasally positioned support for the patient. For the exposures of patients having teeth, the seating part is also advantageously composed of a bite-down part on which the patient bites with his front teeth. In contrast to the known apparatus, the positioning of the patient's head in the region below the center of the face no longer occurs via a chin support but occurs only via the rigid seating part held in a defined position at the carrier, the front teeth resting there against for the patient having teeth missing. For patients with some or all of their teeth, the positioning uses a sub-nasal support. The seating part is thus simultaneously both a seating or, respectively, fixing point as well as a pivot point for the patient's head given alignment to the "Frankfurter Horizontal". In comparison to the known apparatus wherein the forehead support is adjustable both horizontally as well as vertically and the bite-down rod held pivotably therein can be horizontally adjusted, the present invention has only the forehead support which is adjustably arranged and this is only adjustable in the horizontal direction. Apart from the bite anomalies wherein an adjustment of the seating parts may be necessary, the seating part is in a fixed position. The positioning of the patient's head is thereby also simplified. The patient is first sub-nasally or frontally fixed with the incisors on the seating part and with the possible assistance of a light beam positioner, he is subsequently adjusted to the "Frankfurter Horizontal". At this time, the forehead support is merely moved horizontally toward the patient until it presses against the patient's head. The value indicated in this position is to be registered to perform reproducible exposures.

Dependent on whether a standard, a sinus or a maxillary joint exposure is to be produced, a seating part differing in length and depth dimensions which does justice for the different types of exposures, i.e. splice positions, can be inserted into the carrier. Alternatively, the carrier can also be arranged adjustable by appropriate length and depth dimensions so that standard as well as sinus or, respectively, maxillary joint exposures can be produced with one and the same seating part. Advantageously, the carrier can have an eccentrically mounted cylindrical drum, or the like, on whose circumference a plurality of acceptance devices in the form of bores, pegs, slots or the like are provided so that the seating part for the front teeth or, respectively, the sub-nasal seating part in accordance with the above mentioned different splice positions is achieved by means of the eccentric arrangement.

For maxillary joint exposures, wherein an exposure given an open patient mouth (open bite) and given closed mouth (closed bite) should be produced in order to recognize the articulate space better, it is advantageous to provide different bite-down parts which define the open angle of the patient's mouth. It is especially advantageous when a spacer part or spacing member, which defines the opening angle for an exposure with an open bite, is arranged at the same time at that bite-down part with which the exposure for the closed bite is produced. This spacer part is brought into a retracted position for a further exposure with the closed bite after the exposure with the open bite has been produced without having to change the positioning of the patient. Both exposures are thereby produced in an immediate succession without changing the patient's positioning. The spacer part can be held at the seating part in a pivotable, hingeable fashion and can also be mounted in a longitudinally displaceable fashion by means of a suitable guide means, for example a dove-tailed guide.

The fixing for partially toothed or toothless patients occurs sub-nasally, for example, immediately below the nose of the patient at the sub nasal point. A member or part fashioned appropriately for this purpose is again rigidly arranged on the carrier in a defined position and can, as already set forth, be differently designed in length and depth for the different types of exposures (standard, sinus and maxillary joint exposures) or can be securable to a mount arranged appropriately adjustable. It is advantageous to arrange the mount of the seating part above the plane of the teeth, for example, at the forehead support itself, so that imaging of the part on the exposures are avoided.

In order to be able to produce reproducible exposures, wherein the occlusion is to be checked, it is proposed that a combined hinged and pivot means which contains a bite-down plate be provided at the carrier to which the seating part, for example the bite-down part or the sub-nasal seating rod, is secured. A fixing of the patient's head is capable of being carried out with the bite-down plate together with the forehead support as set forth so that after the patient's head has been fixed or positioned, the bite-down plate can be released by the patient and then can be pivoted or, respectively, hinged out of the patient's mouth by means of the pivot device and subsequently out of radiation or, respectively, the exposure region without having to thereby adjust the upper jaw. After the bite-down plate has been removed, an exposure with a true-closed bite, i.e. without an intervening bite-down part no matter how thin, can be carried out.

Other advantages, developments and improvements of the invention will be readily apparent from the following description, the drawings and claims.

DESCRIPTION OF THE PREFERRED EMBODIMENTS

Figure 1:
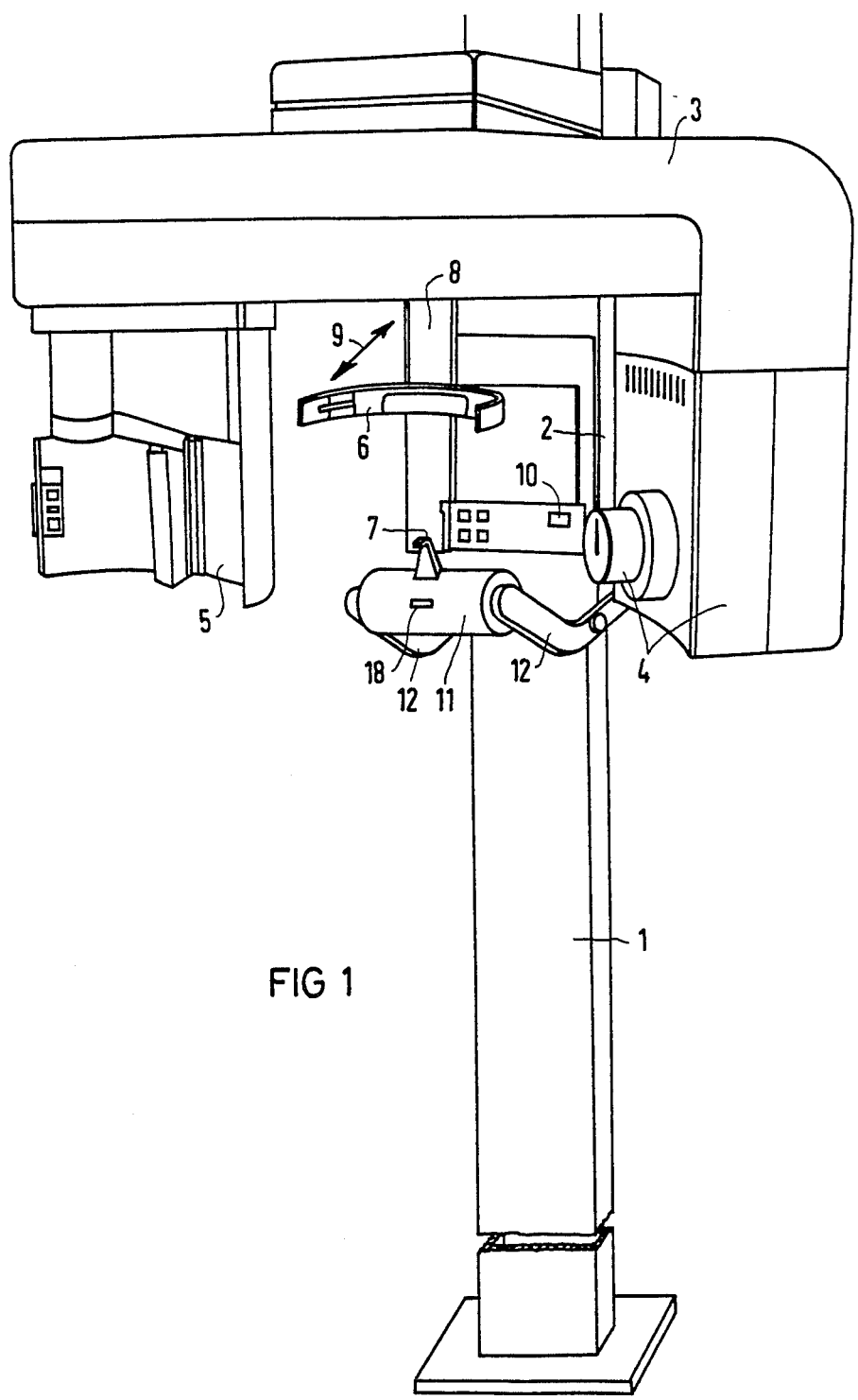
FIG. 1 is a perspective view of an x-ray diagnostic installation in accordance with the present invention.

The principles of the present invention are particularly useful when incorporated in a dental x-ray diagnostic installation illustrated in FIG. 1 for producing panoramic slice or strip exposures. The installation or apparatus includes a pillar 1 on which a bogie truck 2 is arranged adjustably in the vertical height direction. A rotary unit 3 is secured to the bogie truck 2 and carries an x-ray source 4 and a film cassette 5 in a known manner. The structure and functioning of the parts 4 and 5 are conventional.

For the purpose of positioning the patient's head, a forehead support 6 is first provided and a second positioning device including a seating part 7 is also provided. The forehead support 6 is secured to the rotary unit 3 by means of a vertical carrier 8 and is horizontally adjusted in the direction of the arrow 9 with the adjusted position being displayed digitally on a digital display 10.

The seating part 7 is removably secured to a cylindrical carrier 11. The carrier 11 is eccentrically mounted in a pivotal fashion between a pair of retaining arms 12 which in turn are connected to opposite surfaces or sides of the bogie truck 2. The carrier 11 can be pivoted in the arms 12 between two definite latching positions.

Figure 2:
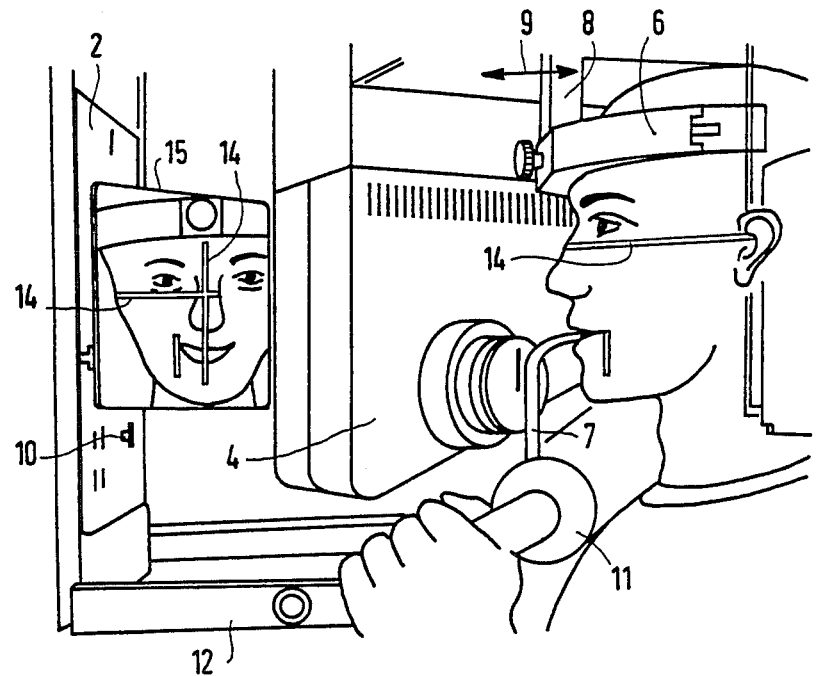
FIG. 2 is an enlarged perspective view of a portion of the apparatus of FIG. 1.
Figure 3:
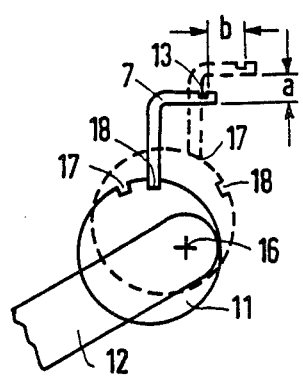
FIG. 3 is an enlarged end view of a carriage supporting a seating part with a second position of the carriage and seating part being illustrated in broken lines.

As best illustrated in FIGS. 2 and 3, the seating part 7 is a curved member having a free end which is insertable into a patient's mouth as illustrated in FIG. 2. The free end contains a notch or elevation which forms a seating surface for seating the front teeth of the patient. In FIG. 3, the seating surface is formed by a notch 13.

Before fixing the patient's head, the overall rotary unit and thus the seating part 7 are aligned to a height position corresponding the size of the patient and are thus aligned by adjusting the vertical position of the bogie truck 2 on the column 1. After this has been accomplished, the patient places his front teeth against the seating surface formed by the notch 13, and the patient's head is now aligned relative to the "Frankfurter Horizontal" and has his face centered. This alignment is accomplished with the assistance of a known light beam localizer or positioner which has light rays in a pattern 14. The positioning is further aided by the assistance of a mirror 15. The notch into which the front teeth engage thus forms a pivot point around which the patient's head is rotated until it is aligned relative to the "Frankfurter Horizontal". After the alignment of the head, the forehead support 6 is adjusted in the direction of arrow 9 until it is firmly seated against the patient's head. The value thereby displayed on the display 10 is noted for later positioning to take reproducible exposures.

In order to also be able to make the initially explained sinus and maxillary joint exposures in addition to the standard exposure, the seating parts, which have different height and depth dimensions, are to be provided to obtin different height and lateral dimensions a and b or the seating part is used but relocated in the carrier which may also be moved between positions. As a consequence of the different levels for standard exposures thus for either sinus or maxillary joint exposures, the seating part for a standard exposure must be dimensioned about 20 through 22 mm larger than the part for sinus or, respectively, maxillary exposures. In order to compensate for these deviations and dimensions, the carrier 11 preferably has a form of a cylindrical drum and is eccentrically mounted by means of the axial bearing 16. The eccentric mounting is mated to the diameter of the drum 11 so that the required position for the standard exposure, as illustrated in broken lines, is achieved when the seating part 7 is inserted or plugged into a first acceptance opening 17 and that the seating position for the sinus and maxillary joint exposures, which is illustrated in bold lines, is achieved when the part 7 is plugged or inserted into a second acceptance opening 18.

Slots, pegs, or the like can also be provided instead of the acceptance opening 17 and 18 for the seating part 7. In any case, however, it is assured that the seating part is held in a precise position on the carrier, which is defined by detents and is secured against twisting. An exemplary embodiment of such a mount will be set forth in greater detail.

In order to have an exact position of the two pivot positions, the eccentric seated drum is provided with a catch means (not shown). In order to avoid a misadjustment or, respectivley, misexposure due to an incorrect positioning/exposure combinations, it also may be equipped with electrical contact protection.

Figures 4, 5:
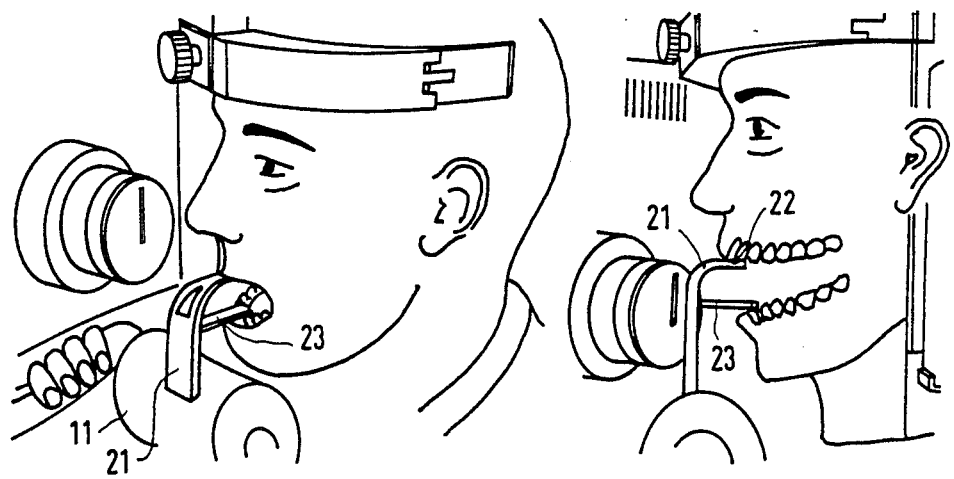
FIGS. 4–7 illustrate an embodiment of a seating part which can be used for maxillary joint exposures with FIG. 4 being a perspective view of the seating part holding the jaw in an open position, FIG. 5 being a side view of the seating part of FIG. 4, FIG. 6 being a cross sectional view of an embodiment of a seating part while in a retracted position, and FIG. 7 being a cross sectional view with the seating part of FIG. 6 in an extended or exposed position.

Embodiments of the seating part 7 are illustrated in FIGS. 4 through 8. In a maxillary joint exposure, two exposures are usually produced; one with an open bite, i.e. with the patient's mouth open, and a second exposure with a closed bite with the patient's mouth closed. A seating part 21 of FIGS. 4 and 5 is held in the carrier 11 for this purpose and is curved towards the patient's mouth similar to the seating part 7. An upper end which is introduced into the patient's mouth contains a notch 22 (FIG. 5) for receiving the front top incisors of the patient. The seating part 21 further contains a distancing or spacing element 23 which provides a defined spacing corresponding to the desired opening angle for the jaws during an exposure with an open bite. The element 23 can be hinged out of a nonemployed or retracted position into an employed or extended position illustrated in FIG. 5.

Figures 6, 7:
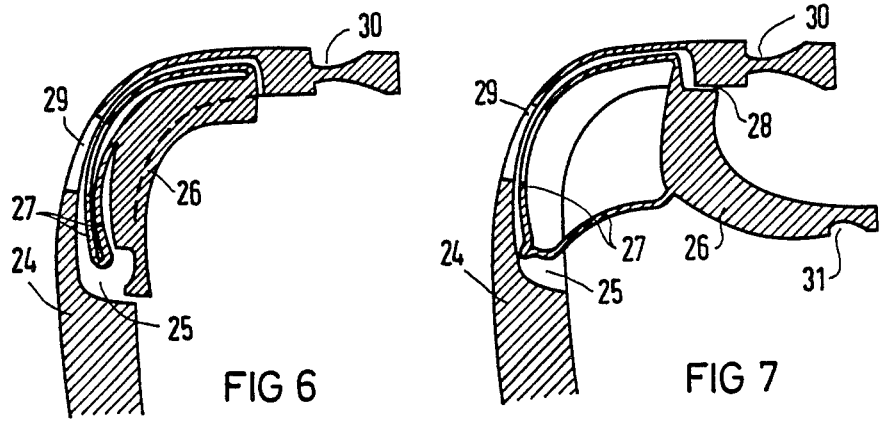

FIGS. 6 and 7 are cross sectional views which show an advantageous embodiment of a seating part 24 wherein in FIG. 6, the distancing element or spacing member 26 is in a retracted position and in FIG. 7, it is shown in an employed or open position. The seating part 24 contains a recess 25 in the region of the curvature for the acceptance of the distancing member 26 which member is roughly adapted to the curvature and also contains two parts 27 forming a flap hinge which enables the distancing member 26 to be brought into a hinged-in position or retracted position as illustrated in FIG. 6. In a similar manner, the hinge arrangement 27 allows the part 26 to be pivoted out to the extended or employed position as illustrated in FIG. 7. In its hinged-out or employed position, the distancing member 26 has a portion which engages a surface 28 of the seating part 24 so that a definite position is established. In order to move the member 26 from the retracted position illustrated in FIG. 6 to the extended position of FIG. 7, the member 26 has an aperture 29 which extends through a portion of the curved and also a portion of the hinge 27 to enable pivoting the member 26 from the retracted to the extended position. The member 24 has a seating surface formed by a depression or groove 30 for the upper front teeth while the member 26 has a groove 31 for receiving the teeth of the lower jaw.

Figure 8:
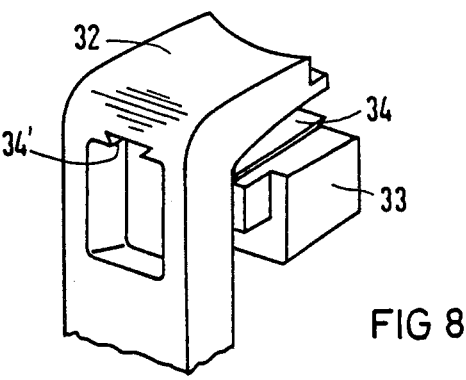
FIG. 8 is a perspective view of another embodiment of a seating part for maxillary joint exposures.

An alternate solution is illustrated in FIG. 8. In this position, a distancing part or member 33 is slidably moved on a seating part 32 by means of a dove-tailed projection 34 being received in a dove-tailed groove 34'. Thus, the member 33 can be moved to a position to provide the positioning surfaces for making an open bite and then shifted in the dove-tailed groove 34' to a retracted position to enable a closed bite. A notch or respective elevation defining a seating surface for the front teeth is again provided on the member 32.

Figure 9:
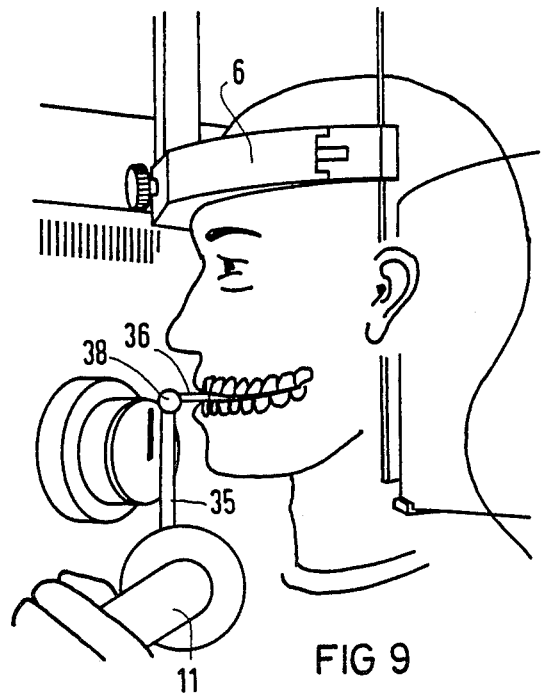
FIG. 9 is a side view of an embodiment of a seating part for a bite-down operation.
Figure 11:
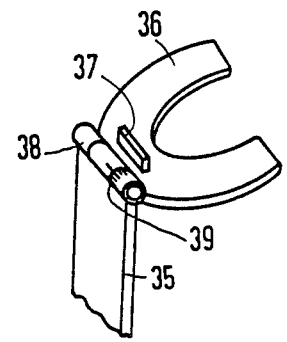
FIG. 11 is a perspective view of the seating part of FIG. 9.
Figure 10:
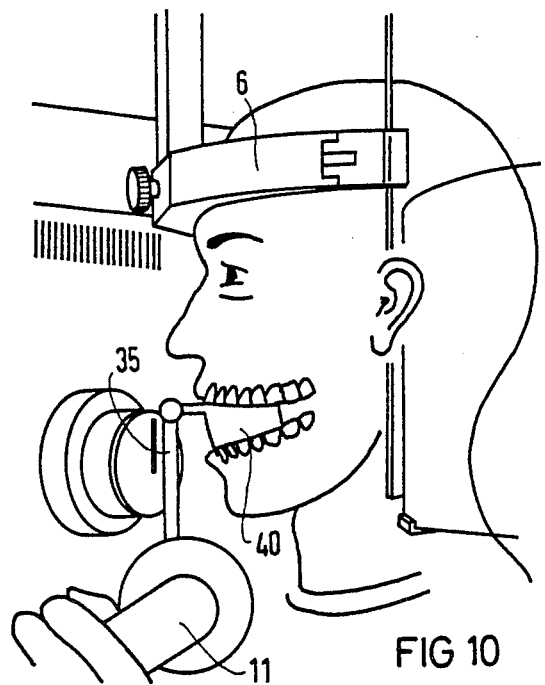
FIG. 10 is a side view of a modification of a seating part for holding the jaw in an open position.

Additional embodiments of the seating part are illustrated in FIGS. 9 through 11. As illustrated, a seating part 35 has an end 36 which faces the patient's mouth and is fashioned as a bite-down plate as best illustrated in FIG. 11. This bite-down plate again includes a seating surface 37 for the front teeth of the patient and is illustrated as being a elevation or projection; however, a depression can also be utilized. In contrast to the previous embodiments, the positioning herein occurs upon the occlusion plane wherein the bite-down plate 36 is flexibly connected to the remaining part of the seating part 35 by a hinge-like articulation of a pivot connection 38. Moreover, a marking or scale 39 (FIG. 11) which serves the purpose of being able to register the angular position between the bite-down plate 36 and the part 35 are provided on portions of the hinge or pivot connection 38. Thus, the setting or position can be reproduced to attain reproducible exposures. As illustrated in FIG. 10, a corresponding distancing member 40 can be provided for exposures for the open bite. In this embodiment, the articulate connection 38 is designed such that the bite-down plate 36 (FIG. 9) can be easily replaced by the spacing member 40 and vice versa.

Figure 12:
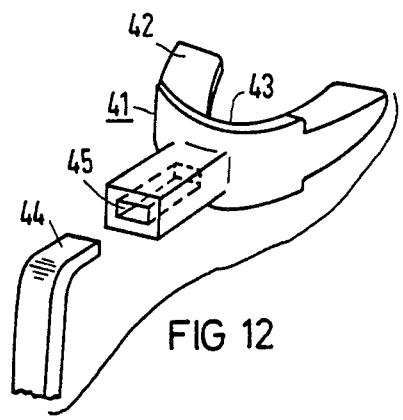
FIG. 12 is a perspective view of a partially disassembled embodiment of a seating part.

In the embodiment illustrated in FIG. 12, the seating part 41, which again contains a bite-down plate 42 as well as seating surfaces for the front teeth formed by an elevation 43, can be put in place on a curved rod 44. As mentioned earlier with regard to the seating part 7 held on the carrier 11 of FIG. 1, so that an exact, defined position of the part is established relative to one another, the curved rod 44 comprises a profile at its free end which deviates from a circular form and the part 41 has a corresponding fashioned acceptance opening or socket 45 having a definite depth detent. Given this modification when the patient first introduces the seating part 41 into his mouth and bites firmly down observing the incisor detents, the patient can subsequently, insert the part onto the curved rod 44 by plugging the end of the rod 44 into the socket 45.

Figure 13:
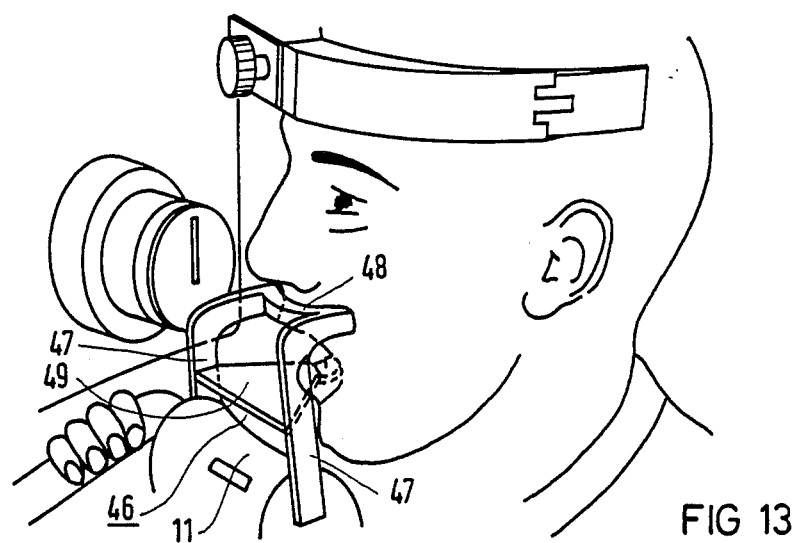
FIG. 13 is a perspective view of an embodiment of a seating part for partially toothed or, respectively, toothless patients.
Figure 14:
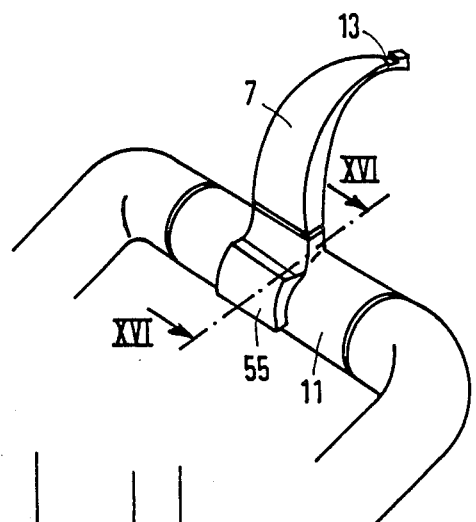
FIG. 14 is a perspective view of an embodiment of a mount for a seating part.

When a patient only has part of their teeth or is completely toothless, a seating part 46 illustrated in FIG. 13 is provided. The seating part 46 has a shackle configuration with a pair of legs 47 interconnected by a web 48. The two legs 47 can be introduced in corresponding acceptance bores in the carrier 11 with the introduction defining the particular position. In addition, they can be held in definite positions at the side of the carrier 11. The web 48 is fashioned so that it forms a subnasal seating surface for the patient with the seating surface lying immediately below the nose of the patient. Advantageously, at least that side of the connecting web facing the patient can be provided with a noncompressible seating surface. For a maxillary joint exposure, a distancing element 49 is provided and is capable of being pivoted into an appropriate use position for such open bite exposures. The shackle-like mount has an advantage that the seating part is not co-imaged into the exposure.

Figure 15:
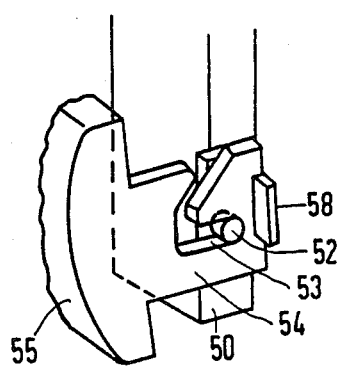
FIG. 15 is a perspective view of a latch arrangement with portions removed for purposes of illustration.
Figure 16:
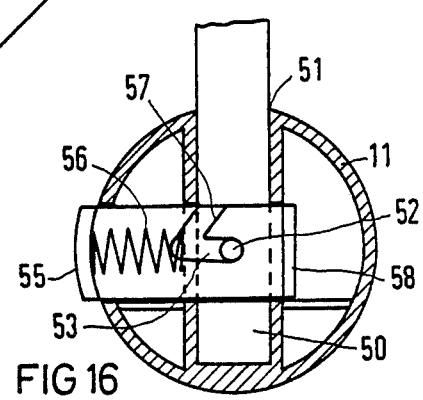
FIG. 16 is a cross sectional view with portions in elevation for purposes of illustration taken along line XVI—XVI of FIG. 14.

As mentioned hereinbefore, the seating of a part, such as 7, in the carrier 11 can be accomplished with the following construction. The seating part 7 on an end 50 which is opposite the end inserted into the patient's mouth will have a cross sectional shape other than a circular shape, for example, a rectangular cross section as shown in FIG. 15. The carrier 11 contains a socket 51 (FIG. 16) which has a matching cross section so that the end 50 can be plugged therein and secured against turning. In its plugged condition, male catch members or pins 52 are arranged to extend from each side of the seating part 7 and are received in slots 53 which are formed in a web 54 of a push button 55. The latch position between the push button 55 and the end 50 are illustrated in FIGS. 15 and 16 and as illustrated in FIG. 16, the latch position is maintained by a spring 56 which urges the push button to the latching position. When the push button 55 is pressed, the latch connection in undone. In order to facilitate forming the latch connection, each of the slots 53 is provided with a entry bevel 57 or curved portion to help engage the pins 52 and move the button into the latching position against the action of the spring 56. Detents or extensions 58 are provided to engage corresponding walls of the carrier 11 to prevent the removal of the push button after the end part 50 has been removed. Thus the detent limits the maximum movement of the member 55 by the spring 56.

Figure 17:
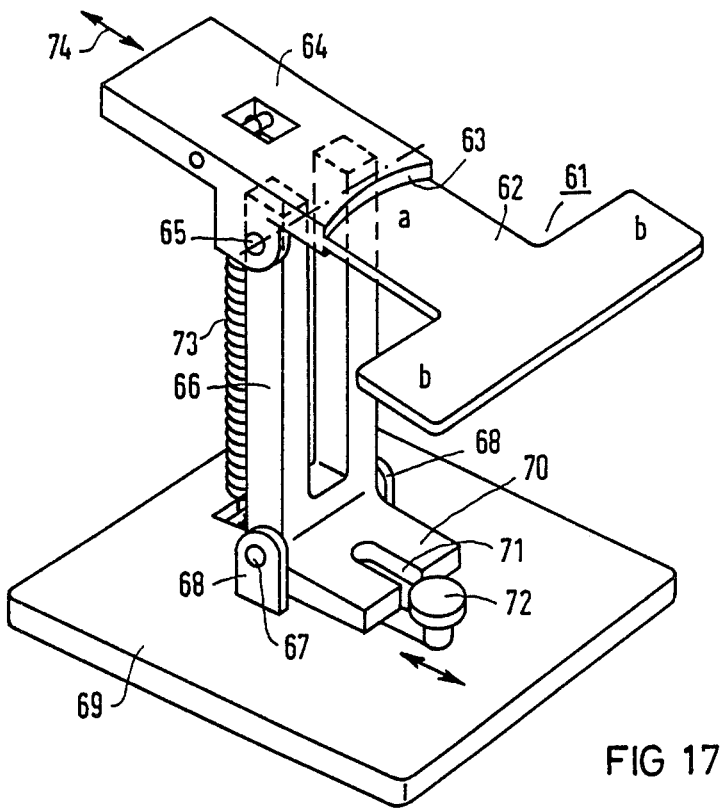
FIG. 17 is a perspective view of an embodiment of a seating part with a mounting device for use in positioning a patient for a true-closed bite exposure.
Figure 18:
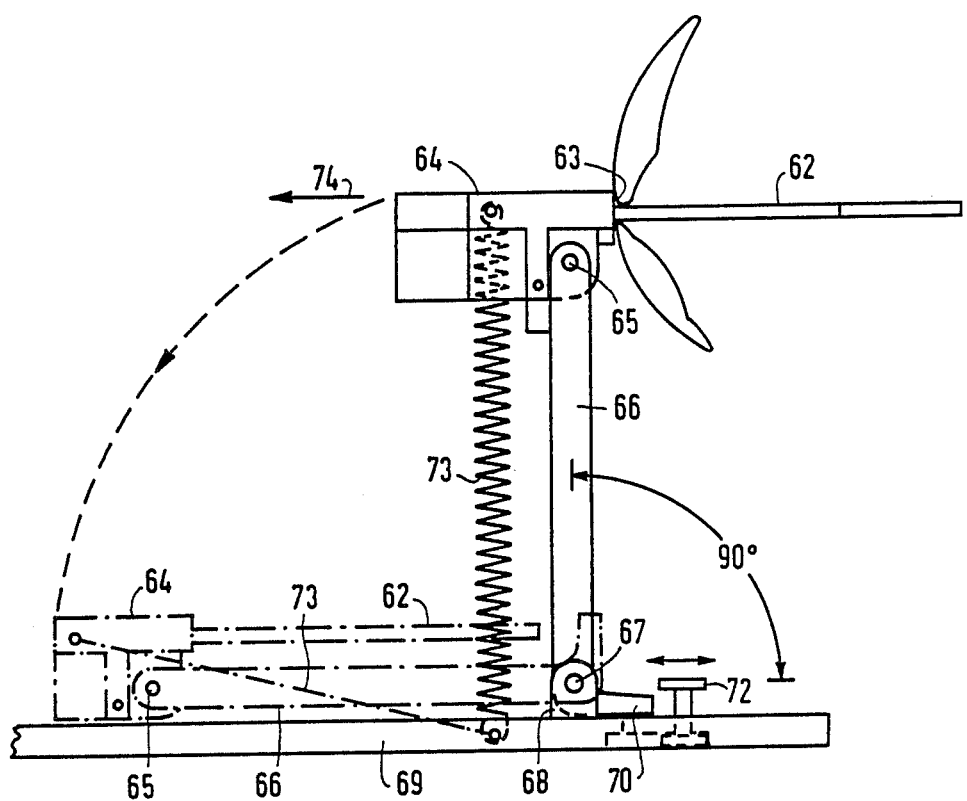
FIG. 18 is a side view of the seating part and device of FIG. 17 with the retracted position shown in chain lines.

An embodiment of the seating part is illustrated in FIGS. 17 and 18 as the seating part 61 which will serve the purpose of producing reproducible exposures with a true-closed bite with the teeth of the upper and lower jaw, pressed directly against one another without changing the position of the head between the positioning assistance of the seating part and the removal of the seating part. The part 61 contains a bite-down plate 62 which is fashioned with a T-shape which forms a three point seat for the teeth. A front tooth being seated against the location a which has an elevation or stop surface 63 and the molars are engaged in the areas b. For hygienic reasons, the bite-down plate 62 is releasably held in a mount 64 so that it can be easily interchanged. An articulated arm 66 has its one end held or pivoted to the mount 64 by means of an articulate connection 65 while the other end is hinged to a lateral retaining part 68 of a plate or carrier 69 to form an pivot connection 67. The articulated arm 66 has an angled off portion 70 having a slot 71 in which a headed member 72 can be introduced for clamping the articulated arm in the raised or vertical position illustrated in FIG. 17. A tension spring 73 is connected at one end to the mount 64 and has an opposite end connected to the carrier 69. As best illustrated in FIG. 18, the seating part 61 is first provided in an extended or exposure position shown in bold lines and subsequently is moved into a folded position which is illustrated in chain lines. When in the extended position, which is used for positioning the patient's head, the articulated arm 66 is in a vertical position as illustrated in FIG. 18. The positioning of the patient head as already described occurs in that this position in which the articulated arm is still clamped by means of the latch connection 71,72 so that either a bite-down of the patient on the bite-down plate 62 with the seating of the front teeth against the elevation 63 and the seating of the forehead on the support 6 can be obtained. After the head position has been obtained, the interlock 71,72 is undone. The patient then slightly opens his mouth so that the lower jaw moves slightly down away from the bite plate 62. In the arrngement of the parts, the spring guarantees that the bite-down plate 62 remains in the adjusted position with the perpendicularly positioned articulated arm 66 even when the interlock 71,72 are released. Then with a slight movement of the mount 64 in the direction of the arrow 74, the articulated arm 66 will pivot around the axis of the articulated joint or connection 67 so that the bite-down plate is moved out of the patient's mouth and is simultaneously moved somewhat downward so that the upper jaw is thereby not touched and the position of the upper jaw which was previous set is retained. As a consequence of the effect of the spring 73, the apparatus as shown in FIG. 18 in the folded position with such a degree that the articulated arm and bite-down plate no longer lie above one another. In this position, the patient can now complete a closed bite and is ready for an exposure of this closed bite position.

Figure 19:
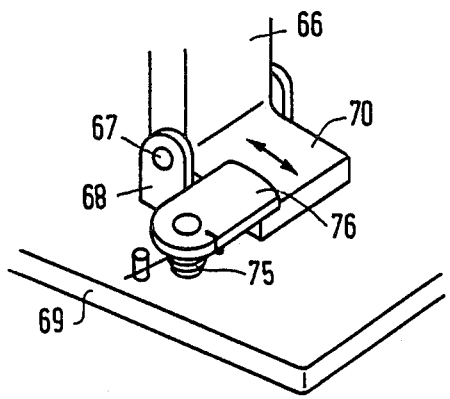
FIG. 19 is a perspective view of a modification of a catch arrangement for the device of FIG. 17.
Figure 20:
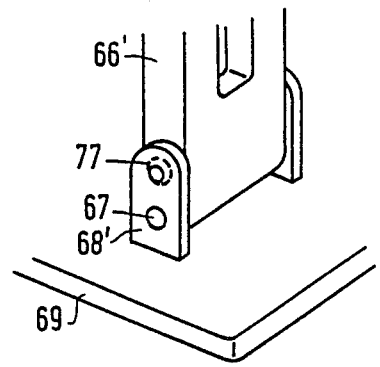
FIG. 20 is a perspective view of another modification of a catch arrangement for the device of FIG. 17.

The fastening of the articulated arm can be carried out in various ways. As illustrated in FIGS. 19 and 20, alternate ways of holding the articulated arm 66 in the raised or extended position are shown. In FIG. 19, a disk 76 is mounted on a pin and held by a spring 75 in an extended position engaging the foot 70. To release the foot 70, the plate is pivoted against the force of the spring 75 to a retracted or disengaged position.

In FIG. 20, the articulated arm 66' does not have the foot 70. The arm does contain ball catches 77 which are provided on both sides. The ball catches 77 will hold the articulated arm in the vertical position by being engaged in depressions or apertures formed in the retaining parts 68' of the plate 69.

Although various minor modifications may be suggested by those versed in the art, it should be understood that we wish to embody with the scope of the patent granted hereon, all such modifications as reasonably and properly come within the scope of our contribution to the art.

We claim:

1. In a dental x-ray diagnostic installation for producing a congruent panorama strip of exposures of a jaw of a patient, said installation containing a pillar and a bogie truck adjustably arranged on the pillar for adjustment in a vertical height direction, a rotary unit secured to the bogie truck and carrying a radiation source and a film cassette and two positioning means for placing a patient's head in position with reference to the rotary unit, one of said two positioning means being a horizontally adjustable forehead support and said installation containing a display means for illustrating an adjusted position of said forehead support, the improvement comprising a carrier being mounted on said bogie truck, each installation only using two positioning means with a second means of the two positioning means providing both a fixing point and a pivot point, said second means being selected from a first seating part having a seating surface for engaging front teeth of a patient and a second seating part having a contact surface for engaging a sub-nasal point of the patient, both the first and second seating parts having mounting means and said carrier having a first acceptance device for receiving the mounting means to hold the selected seating parts without rotation in a rigid defined position on the carrier so that it is possible to make exposures of both patients who have all of their teeth and patients who do not have all of their teeth by changing from the first to the second seating part.

2. In an installation according to claim 1, wherein the carrier is adjustably mounted on the truck by support means allowing movement between a first position for standard exposures and a second position for permitting maxillary joint exposures, said carrier having a second acceptance device for mounting the first seating part in a second location spaced both horizontally and vertically from a first location when in the first acceptance device.

3. In an installation according to claim 1, wherein the first seating part is provided with a spacing member for holding the patient's mouth in an open condition, said spacing member being carried on the first seating part and being movable on the first seating part from a retracted position in which the first seating part serves for exposures with closed patient mouths to an employed position for exposure with an open mouth.

4. In an installation according to claim 1, wherein the first acceptance device includes mean for holding the selected seating part, said means for holding including an interlock being shifted to a disengaging position by a push button.

5. In an installation according to claim 3 wherein to form the retracted position, the first seating part has a recess for receiving the spacing member, said spacing member being pivotably connected by an articulate connection to the first seating part so that it can be pivoted between the retracted position and the employed position.

6. In an installation according to claim 5, wherein the first seating part is a curved part having a free end curving towards the patient's mouth and provided with a seat for the front teeth of an upper jaw, said spacing member having a free end likewise containing a seat for the front teeth of a lower jaw, said spacing member being held in the employed position with a surface of the spacing member engaging a stop face on the first seating part.

7. In an installation according to claim 6, wherein the first seating part has an aperture to enable access for moving the spacing member from the retracted position to the employed position.

8. In an installation according to claim 3, wherein the spacing member is slidably held on the first seating part by means of a plug-in connection provided with guide means.

9. In an installation according to claim 1, wherein the second seating part has a shackle shape with a pair of legs with a connecting web, said second seating part being connected to the carrier by said pair of legs and said connecting web forming a seating surface adapted to a mouth shape in a sub-nasal point for engaging a patient having at least part of his teeth missing.

10. In an installation according to claim 1, wherein the first seating part utilizes a bite-down plate provided with a seating surface for front teeth and surfaces for engagement by at least one molar on each side to form a three point seating.

11. In an installation according to claim 10, wherein said bite-down plate is connected by a pivotal connection to an arm secured on the carrier, said pivotal connection having a horizontal axis and being provided with markings to indicate a pivoted position between the bite-down plate and said arm.

12. In an installation according to claim 10, which includes mounting means for securing the bite-down plate on said carrier, said mounting means including a mounting member for releasably securing the bite-down plate to the mounting means, said mounting means including a hinged-swivel arrangement having an articulated arm having one end connected to the carrier for pivotal movement between a vertically aligned position and a retracted horizontal position, a second end of said arm being pivotally connected to the mounting member for the bite-down plate and a force element arranged between the carrier and said mounting member to hold the arm against a stop while in the vertical position, said force element urging the arm and mounting member to a retracted pivoted horizontal position when the arm and mounting member are moved away from said stop after release of the bite-down plate by the patient's jaw so that a completely closed bite exposure can be made.

13. In an installation according to claim 12, wherein the lower end of the articulated arm is fixably held in the vertical position by means of a quick-release clamping device, said arm being provided with an angle foot and said clamping device engaging said angle foot.

14. In an installation according to claim 1, wherein the carrier is a cylindrical drum eccentrically mounted on retaining arms connected to said truck, said drum containing at least first and second acceptance devices for receiving the first and second seating parts and being rotated on the eccentric mounting to present different acceptance devices for mounting the seating part in different positions for different types of exposures so that standard, sinus and maxillary joint exposures can be obtained.

15. In an installation according to claim 14, which includes means for holding the drum in various eccentric positions for various types of exposures.

16. In an installation according to claim 4, wherein said means for holding comprises an end of each seating part having a cross section deviating from a circular shape, and said carrier having a socket corresponding to said shape for receiving the end of the seating part in the carrier, said interlock comprising a carrier member being movable at right angles to an axis of the socket between a first and second position, a spring urging the carrier member toward the first position, said carrier member having a detent engaging a wall of the socket to define the first position, said end of the seating part having at least one locking pin extending from a surface and said carrier member having a catch slot with a curved entrance for receiving the pin to form an interlock between the part and socket, said push button shifting the carrier member against the spring to enable disengagement between the pin and catch slot.

* * * * *